United States Patent
Takei et al.

[11] Patent Number: 6,150,461
[45] Date of Patent: *Nov. 21, 2000

[54] CARRIERS TARGETTABLE TO ORGAN

[75] Inventors: Yoshiyuki Takei, Suita; Atsushi Maruyama, Yokohama; Toshihiro Akaike, Hoya; Sunao Kawano, Ashiya; Shigetoshi Okumura, Nara; Masayuki Nogawa, Tama; Shoichiro Asayama, Kamakura, all of Japan

[73] Assignees: Hisamitsu Pharmaceutical Co., Inc.; Rohto Pharmaceutical Co., Ltd., both of Japan

[*] Notice: This patent issued on a continued prosecution application filed under 37 CFR 1.53(d), and is subject to the twenty year patent term provisions of 35 U.S.C. 154(a)(2).

[21] Appl. No.: 08/863,564

[22] Filed: May 27, 1997

[51] Int. Cl.[7] .......................... C08G 63/48; C08G 63/91; A61K 38/14; C07K 1/00
[52] U.S. Cl. .......................... 525/63; 525/54.1; 525/54.2; 525/54.11; 527/200; 527/207; 530/322; 530/395; 514/2; 514/8
[58] Field of Search ..................... 530/322, 395; 514/2, 8; 525/54.11, 54.1, 54.2, 63; 527/200, 207

[56] References Cited

U.S. PATENT DOCUMENTS 4,908,404  3/1990  Benedict et al. .............. 525/54.11
5,523,222  6/1996  Page et al. ................... 435/172.3

OTHER PUBLICATIONS

Ferkol, T. et al. Regulation of the Phospholpyruvate Carboxykinase/Human Factor IX Gene Introduced into the Lives . . . FASEB J. vol. 7, 1081, Aug. 1993.

Cera, C. et al. Water–Soluble Polysaccharide–Anthracycline Conjugates: Biological Activity Anti–Cancer Drug Design, vol. 7 143, Nov. 1992.

Mikawa, M. et al. (1996). "Application of Receptor–Directed Glycopolymers for Magnetic Resonance Imaging Contrast Media." Fifth World Biomaterials Congress, May 29–Jun. 2, 1996, Toronto, Canada.

*Primary Examiner*—Nancy A. Johnson
*Assistant Examiner*—Lin Sun-Hoffman
*Attorney, Agent, or Firm*—Rothwell, Figg, Ernst & Manbeck, p.c.

[57] ABSTRACT

A carrier for delivering a foreign substance to a target organ which comprises a graft copolymer in which hyaluronic acid is grafted on a polymer composing main chain, wherein the main chain has a part capable of binding to the foreign substance electrostatically, and contains one or more monomer unit having side chain with amino or imino group capable of coupling to hyarulonic acid, which is useful for delivering a foreign substance to a target organ, especially liver.

16 Claims, 11 Drawing Sheets

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 1
tactgtcgtc gtcccctcaa                                           20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 2
ataactgccg tcactccaac                                           20

CARRIERS TARGETTABLE TO ORGAN

FIELD OF THE INVENTION

The present invention relates to a carrier useful in the field of clinical medicine. In particular, it relates to a carrier for delivering a foreign substance to a target organ which comprises a graft copolymer in which hyaluronic acid (HA) is grafted on a polymer main chain, wherein the polymer has a part capable of binding to the foreign substance electrostatically, and contains one or more monomer unit having side chain with amino or imino group capable of coupling to hyarulonic acid (hereinafter, the said polymer main chain is referred to as PAA and the said graft copolymer is referred to as HA-g-PAA copolymer or PAA-g-HA copolymer). Specifically, the present invention relates to a carrier useful in vivo for delivering a foreign substance to a target organ, especially, to liver. It also relates to a complex targettable to an aimed organ, which is formed between a HA-g-PAA copolymer and a foreign substance to be delivered to a target organ.

DESCRIPTION OF RELATED ART

As the rapid improvement of the gene technology, various molecular biological techniques have been developed so far. Concurrently, the analysis of genetic information as well as the elucidation of genetic function have greatly progressed. Under the conditions, many attempts have been made to apply the fruits of the researches to various fields of clinical medicine. The gene therapy is one of the fields that have been attained the greatest progress. As a result of the identification of causative genes of various genetic diseases and elucidation thereof, the gene therapy is no more in the basic experimental stage but in the practical stage. For example, the RAC of the National Institute of Health (NIH, USA) accepted 81 protocols of gene therapy till June 1995, and clinical trials have already been carried out for over 200 patients suffering from genetic diseases such as congenital immunodeficiency syndrome, familial hypercholesterolemia, cystic fibrosis, and the like, and various cancers (Jikken Igaku Vol. 12, No. 3, 303–307, 1994).

The gene therapy is expected to be a useful method capable of treating a disease at the cell level though, there are some technical problems to be solved. Thus, one problem is that how a foreign gene can be introduced into a target cell efficiently and safely. To solve the problem, virus vectors usable as a (gene) carrier have been provided.

Examples of such vectors include virus vectors originated from retro virus such as mouse leucovirus (Moloney Murine Leukemia Virus, MLV), adenovirus, herpesvirus, HIV, adenovirus-associated virus (AAV) and the like.

MLV is an RNA virus with envelope and invades into a cell through the binding between the envelope protein and a receptor on the cell surface. After invasion, the single-stranded virus RNA is converted into a double-stranded DNA, which is then integrated into the genome DNA of the infected cell. The integration via the retrovirus vector, however, requires that the target cell is dividing and growing and therefore is not effective unless the target cell is under dividing. Accordingly, the efficiency of the delivery system using retrovirus vector is very low when the target cells are those generally in the resting phase, such as hepatocytes.

Recently, much attention has been paid to adenovirus vector which can be used to introduce a gene into non-dividing cells. However, by the use of adenovirus vector, a foreign gene cannot be integrated into the genomic DNA of the target cell and therefore the effect of gene therapy could lapse within several weeks or several months at the longest. Accordingly, one must repeat the insertion procedure often, which possibly causes problems, for instance, the increase in the physical and mental burden on the patient, decrease in the efficiency of gene introduction due to the production of anti-adenovirus antibody. Further, inflammatory reaction attributable to the imunogenicity and cytotoxicity of adenovirus particles were observed during the clinical trial that has recently been started, where adenovirus vector was administered bronchoscopically for the treatment of cystic fibrosis.

Herpesvirus vector is expected to be useful to introduce a foreign gene into nerve cells though, there has been no progression in the development thereof because it is highly cytotoxic and has an extremely big genome size, i.e., 150 kb.

HIV vector has been developed as a vector capable of specifically introducing a foreign gene into CD4 positive T-lymphocyte owing to the host specificity of the virus itself (Shimada T., et al., J. Clin. Invest. 88, 1043, 1991). However, the most notable drawback of the HIV vector is that the introduction of the vector could be accompanied by the contamination by wild strains.

AAV vector has been expected to be useful for integrating a gene into a targeted site on chromosome because AAV of wild-type is known to be integrated into a specific site of the No. 19 chromosome. However, a recent research revealed that the recombinant vector lacks the said characteristic and therefore a foreign gene is randomly integrated into chromosome. Further, there is a limitation in the size of foreign gene, that is, the vector can afford to carry a gene of less than 5 kb.

There have been proposed many approaches for gene therapy using various gene-introducing systems involving the use of artificial carriers other than virus vector. For instance, gene-lipid complex between a gene and positively charged lipid was developed as a non-viral carrier for gene therapy. The said carrier, however, has drawbacks such as cytotoxic effect depending on the dose and therefore cannot be administered in a large amount. In another approach, many researchers proposed, taking advantage of the electric property (negative charge) of nucleic acids and its derivatives, to prepare an electrostatic complex between a nucleic acid or its derivative and a synthetic polymer derivative with positive charge and then deliver the complex to/into a target cell (Bioconjugate Chem., Vol. 3, 323–327, 1992; Proc. Natl. Acad. Sci. USA, Vol. 89, 7934–7938, 1992; J. Biol. Chem., Vol. 269, 12918–12924, 1994; Japanese Patent Publication (Kohyo) Nos. 6-505980, 6-507158). However, synthetic polymers have been known to be highly cytotoxic when used alone (Bioconjugate Chem., Vol. 1, 149–153, 1990). Further, upon administration, such a synthetic polymer could be recognized as a foreign substance and affect immune system to cause immunoreaction such as anaphylactic shock.

On the other hand, the use of nucleus protein which could hardly be recognized as a foreign substance has been attempted. Nucleus protein has an ability to specifically bind to a nucleic acid and its derivative, which might render the nucleus protein useful as a gene vector. For example, one of nucleus proteins, histone, was used as a carrier for plasmid DNA (Yasufumi Kaneda et al., Science, Vol. 243, 375–378, 1989; Mirjam Breeuwer and David S. Goldfarb, Cell, Vol. 60, 999–1008, 1990; Jian Chen et al., Human Gene Therapy, Vol. 5, 429–435, 1994).

Polymeric cations such as polyamines or polymers composed of basic amino acids, e.g., polylysine, are known to be useful as carriers for DNA. In the case of polyamines, multivalent-protonized polyamines do not show sufficient stabilizing effect under the physiological conditions. There are additional problems, for instance, triple-stranded DNA is very labile under the physiological conditions, inter-calater stabilizes mainly double-stranded DNA but not triple-stranded DNA, and the like. Polymers composed of basic amino acids, which are a kind of polymeric cations, show stabilizing effect through the strong binding to DNA which leads to the reduction of the repulsion between phosphate groups. However, polylysine cannot be used alone to form a complex with DNA in the form of double- or triple-stranded DNA, because it does not recognize any particular DNA and the reaction results in the agglutination and precipitation of products.

As mentioned above, the method for introducing gene using existing carriers including virus vectors has various problems in terms of the introduction efficiency, safety, and the like.

Recently, interests have been centered to the establishment of a method of delivering efficiently a foreign substance such as a drug or gene to target cells so as to treat a subject safely and effectively. In the case where the foreign substance is a gene, it is desirable that the said gene is incorporated in the target cells and expressed. For such purposes, many approaches have been made to obtain carriers capable of delivering a foreign substance to a target organ(s) to be treated. One of such approaches involves the modification of a vector by ligating thereto a substance, e.g., sugar chains, which recognizes an intended organ. Carriers for drug delivery system (DDS carrier) aimed at liver have been developed, which comprise a vector to which a substance capable of specifically binding to asyaloglycoprotein receptors present on hepatic cells (parenchymal cells) is attached. Examples of such DDS carriers include polystyrene derivatives having t-galactose side chain, or polylysine to which asyaloglycoprotein is attached. These carriers have proved to have ability to deliver a foreign substance to liver efficiently (A. Kobayashi, M. Goto, K. Kobayashi, T. Akaike, J. Biomater. Sci. Polym. Ed. 6, 325, 1994; G. Y. Wu., C. H. Wu, J. Biol. Chem., 262, 4429, 1987). However, they have not been put to practice yet for some reasons.

Although the DDS targeting liver has been focused on the delivery of a drug to parenchymal cell so far, recent researches revealed that the sinusoidal endothelial cell (SEC) plays an important role in the pathogenesis of liver diseases. Takei, Y., et al., Transplantation 51, 959–965 (1991); Oshita, M., et al., Hepatology 16, 1007–1013 (1992); Mochida, S., et al., Gastroenterology 99, 771–777 (1990); Oshita, M., et al., J. Clin. Invest. 91, 1337–1342 (1993); Nishimura, Y., et al., Transplantation, 61, 99–104 (1996); Mantovani, A., et al., FASEB J. 6, 2591–2599 (1992); Gerristen, M. E., et al., FASEB J. 7, 523–532 (1993); Pober, J. S. et al., Transplantation 50, 537–544 (1991); Bach, F. H. et al., Nature Med. 1, 869–873 (1995); Bach, F. H. et al., Immunol. Rev. 141, 5–30 (1994). For example, injury or impaired functions of SECs contributes to various hepatic diseases such as hepatitis, hepatic failure, transplantation immunity, and the like. It has also been found that SECs can be infected with HIV virus via adhesion molecule, CD4, which is constantly expressed on the cell surface. Steffan A. M. et al., Hepatology 23, 964, 1996; Lafon M. E., et al., AIDS 8, 747, 1994; Steffan A. M. et al., Proc. Natl. Acad. Sci. USA, 89, 1582, 1992. Accordingly, there are increasing demands for establishing a DDS specifically directed to SECs to deliver an intended foreign substance such as drug or gene to the cells. Such DDS would contribute greatly to not only the delivery of a foreign substance to SECs directly but also to affect parenchymal cells indirectly through the intimate interactions between sinusoidal and parenchymal cells.

However, the DDSs developed so far are mostly addressed to parenchymal cells and therefore a DDS specific to SECs has been highly demanded.

SUMMARY OF THE INVENTION

The present inventors have intimately investigated with a purpose of solving the problems above and providing a carrier capable of delivering a foreign substance to an intended organ such as liver, especially, SECs, safely and efficiently. In the course of the research, the inventors have utilized the fact that SECs take up certain glycosaminoglycans, in particular, hyaluronic acid (HA), from circulating system via HA receptor-mediated-endocytosis with high efficiency (Smedsrφd, B. et al., Biochem. J. 223, 617–626, 1984; Smedsrφd, B. et al., Biochem. J. 266, 313–327, 1990). This finding led the inventors to an idea to utilize the specific property of HA in the preparation of a carrier targettable to liver. The present inventors then thought of a preparation of a copolymer comprising HA and PAA capable of stabilizing a foreign substance such as a drug or a gene, especially a gene, in vivo. Such a copolymer was expected to serve as a carrier for delivering a foreign substance to liver efficiently and safely. Finally, the inventors obtained a copolymer by grafting HA on PAA. The resultant carrier should be useful to deliver a foreign substance to not only liver but also various organs because HA receptors are widely found on the cell surface of almost all the organs, although only the SECs are known to take up HA.

The preparation and usefulness of one of such graft copolymers has been published by the present inventors (Atsushi Maruyama et al., Synthesis and Characterization of Polylysine-graft-hyaluronic acid Copolymer as Gene Carrier to Liver Endothelial Cells, pp. 468, in Fifth World Biomaterial Congress, May 29–Jun. 2, 1996, Toronto, Canada). The teachings of the publication are herein incorporated by reference.

As is described in the working examples below, the inventors synthesized a graft copolymer (HA-g-PLL) by grafting HA on poly-L-lysine, obtained a complex in which a DNA is bound to the carrier electrostatically, and evaluated the resultant complex as to the ability to be targeted to liver. The experiment revealed that the complex is actually targettable to liver specifically, and taken up by SECs.

Thus, the present invention provides a carrier for delivering a foreign substance to a target organ which comprises a graft copolymer of hyaluronic acid and a polymer main chain, wherein the polymer has a part capable of binding to the foreign substance electrostatically, and contains one or more monomer unit having side chain with amino or imino group capable of coupling to hyarulonic acid. The said polymer main chain and the graft copolymer are, as mentioned above, referred to as PAA, and HA-g-PAA or PAA-g-HA copolymer, respectively.

The present carrier is specifically useful for delivering a foreign substance to the liver.

In one embodiment of the present invention, the PAA contains amino acid or amino acid derivative coupled through peptide bond.

The PAA preferably contains as monomer unit a basic amino acid(s) selected from the group consisting of lysine, ornithine, arginine residues and derivatives thereof.

The PAA also contains a part(s) capable of binding to a foreign substance electrostatically, which part preferably contains monomer unit selected from lysine, ornithine, arginine residues and derivatives thereof to an extent sufficient for the formation of electrostatic binding.

In one of preferred embodiments of the present invention, the carrier is specifically taken up by liver sinusoidal endothelial cell (SEC).

The present invention also provides a complex formed through the electrostatic binding between the HA-g-PAA copolymer above and a foreign substance to be delivered to a target organ.

In one of preferred embodiments of the present invention, the foreign substance is selected from the group consisting of drug, nucleotides including oligo- or poly-nucleotide, and contrast medium.

For purposes of the invention, the term "foreign substance" means a substance to be administered to a subject for preventing, treating and/or diagnosing a disease. The foreign substance can be synthetic or non-synthetic substance such as a drug, DNA of any length and type, contrast medium and the like, subject that it can form a complex with HA-g-PAA copolymer through an electrostatic binding. Therefore, any substance can be used to obtain the complex of the present invention subject that the substance can bind to the carrier via the part capable of participating into the electrostatic binding. For example, in case that the part(s) in PAA responsible for the electrostatic binding is charged positive, the foreign substance preferably has a part charged negative. However, the foreign substance is preferably selected from those not affecting the interaction between HA and HA receptors on cell surface. Thus, HA having a part charged negative, a foreign substance is preferably charged negative so as not bind to HA. If a foreign substance has a part charged positive, it may bind to HA thereby preventing or reducing the formation of electrostatic binding between the said foreign substance and PAA, as well as inhibiting the interaction between HA and HA receptor. However, one ordinary skilled in the art will recognize that cationic- or non-ionic-substance can be used as far as it can form a complex with a carrier obtained using an appropriate PAA, which also falls within the scope of the invention.

BRIEF DESCRIPTION OF DRAWINGS

FIG. 1 shows the structural formula of HA-g-PLL.

FIG. 2 shows the GPC profile showing the molecular weight of PLL-g-HA to be $6.3\times10^4$.

FIG. 3 shows the migration patterns of PLL-g-HA/DNA complexes formed from PLL-g-HA and DNA of various ratios assessed with a gel retardation assay.

FIG. 4 shows the results of the turbidity measurement of PBS solutions containing various ratios of PLL or PLL-g-HA and DNA.

FIG. 5 shows the organ distribution of PLL-g-HA/DNA complex in rat using the radiolabeled pSVβ-Gal.

FIG. 6 shows the distribution of the PLL-g-HA/DNA complex in the liver lobule.

FIG. 7 shows the results of agarose gel electrophoresis after the PCR amplification of the cytosolic fractions of the liver homogenate.

FIG. 8 shows the results of agarose gel electrophoresis after RT-PCR to determine the expression of PLL-g-HA/DNA complex in liver.

FIG. 9 shows histological detection of cells expressing β-galactosidase in the liver lobule 72 h after in vivo transfection.

FIG. 10 shows $^1$H-NMR spectra of the PLL-g-HA copolymer.

FIG. 11 shows the UV-Tm profile of DNA duplex in the presence or absence of PLL-g-HA.

DETAILED DESCRIPTION OF THE INVENTION

A PAA in the carrier of the present invention has a monomer unit(s) having side chain with amino or imino group capable of coupling to hyarulonic acid.

For this purpose, the PAA preferably contains a basic monomer unit(s) such as a basic amino acid residue or a derivative thereof, e.g., lysine, ornithine, arginine, histidine residues or a derivatives thereof; amine such as allylamine or vinylamine; imine such as ethyleneimine or aminomethylstylene. Preferred monomer unit is a basic amino acid residue, and lysine, ornithine, and arginine residues or a derivative thereof are more preferred.

A PAA also has a part capable of binding to a foreign substance electrostatically. Such a part, as mentioned above, is preferably cationic so that it can bind to a foreign substance charged negative thereby avoiding affecting the interaction between HA and its receptor.

Accordingly, the part of PAA responsible to the electrostatic binding with a foreign substance preferably contains monomer unit having a part charged positive to an extent sufficient for the formation of electrostatic binding. Examples of such monomer units are lysine, ornithine, arginine residues and derivatives thereof.

The amino acid contained in the PAA can be in either of D- and L- forms. It also can has a substituent(s) attached to a part of amino groups. Examples of substituents include alkyl group, acetyl group and/or a halogen atom.

Further, the PAA may contain additional part(s) other than a part(s) responsible to the electrostatic binding or a monomer unit having side chain with amino or imino group, subject that the additional part does not affect adversely the formation of electrostatic binding.

The synthesis of PAA can be conducted according to any one of methods known in the polymer chemistry selecting an appropriate conditions depending on the desired polymerization degree.

For Example, poly-L-lysine (PLL) can be prepared in accordance with the teaching in the literature (Rajendra, B. R., et al., Human Genetics 55, 3633, 1980; Lim, F. and Sun, A. M., Science, 210, 908, 1980) using ∈-carbobenzoxy-lysine-N-carboxylic acid anhydride as a unit.

A copolymer of lysine and serine can be prepared by reacting ∈-carbobenzoxy-lysine-N-carboxylic acid anhydride and bynzylserine-N-carboxylic acid anhydride using a primary amine such as polyethylene oxide having an amino residue at one end (M.W. 200–250,00) and the like as a polymerization initiator. The molecular weight of the resultant PAA is not critical though, those having molecular weight ranging from 200 to 50,000 are generally preferred.

The HA-g-PAA as a carrier of the present invention can be prepared using hyaluronic acid or its salt. Hyaluronic acid is distributed widely in cells and tissues of animals such as umbilical cord, skin, synovial fluid, cockscomb, and the like. In the preparation of HA-g-PAA of the present invention, hyaluronic acid obtained by extracting from the tissues above or from the commercial sources can be used. The molecular weight of hyaluronic acid is not critical though, those having average molecular weight of less than 100,000, preferably from 1,000 to 50,000 are suitable in terms of reactivity with PAA and the ability to recognize a target organ. Accordingly, one can treat HA with an enzyme to obtain HA fragments of appropriate molecular weight before polymerization.

The polymerization between HA and PAA can be conducted by, for example, conjugating HA to PAA by a reductive amination reaction. Specifically, HA and PAA are dissolved in a solvent such as borate buffer (pH 8.5) or phosphate buffer (pH 8.3). After the addition of a reductant such as sodium cyanoborohydride (NaBH$_3$CN), the reaction is conducted at about 0 to 50° C. for about 1 hour to 5 days. Organic solvent such as dimethylformamide, dimethyl sulfoxide, or the like can be added to the reaction mixture to control the reaction. Further, the reaction efficiency can be improved when the formation of an ion complex of PAA and HA is prevented by adding an inorganic salt such as sodium chloride, potassium chloride or the like, or elevating the reaction temperature. The resultant copolymer is preferably of a "comb-shape or comb-type" wherein HAs as side chains are grafted on PAA. The copolymer wherein HA is grafted on PLL is herein referred to as HA-g-PLL or PLL-g-HA. To obtain the comb-type copolymer, the reaction is preferably carried out under conditions for coupling reaction. For example, the preparation of such a graft copolymer involves the following processes: the coupling between the reductive terminus of HA and amino residues on PAA such as PLL, formation of schiff's base, followed by reduction to form imino-bond. The quantity of HA used in the coupling reaction with PAA varies depending on the molecular weight of each reactant. However, the reaction can be done using 1 to 60, preferably 1 to 10 equivalents of HA per 1 mole of PAA. The reaction condition should be selected to obtain a PAA-g-HA of an appropriate grafting rate. The grafting rate (%) is expressed as the proportion of total moles of HA grafted on PAA per total moles of individual monomer (mol %) which can be between 0.01 to 50, preferably 0.05 to 25, more preferably 0.1 to 20%. It is also expressed as weight percent (wt %) which shows the proportion of the total weight of HA per total weight of PAA-g-HA, which can be between 5 to 90, preferably 20 to 80%. The grafting rate (%) is calculated according to the formulas below:

$$\text{Grafting rate (mol \%)}=100\times A/B$$

wherein A is the total mole of HA in PAA-g-HA and B is total mole of monomer unit composing the PAA; or $$\text{Weight percent (wt \%)}=100\times C/D$$

wherein C is total weight of HA in PAA-g-HA copolymer and D is total weight of HA-g-PAA copolymer.

As is easily recognized by one ordinary skill in the art, the grafting rate (mol %) and weight percent (wt %) may vary depending on the molecular weight of each reactant and reaction conditions used. Further, about 1 to 50 equivalents of reductant is generally used per 1 mole of HA.

The so produced HA-g-PAA copolymer as a carrier of the present invention can form a stable complex with a foreign substance such as a drug, DNA, contrast medium or the like electrostatically, which is specifically targettable to an aimed organ because of the presence of HA moiety capable of interacting with HA receptor on cell surface. The complex of the present invention is useful for targeting a foreign substance to liver, in particular, SECs.

The complex of the present invention can be prepared by mixing an appropriate amount of carrier and selected foreign substance in aqueous solution. Further, an appropriate inorganic salt such as sodium or potassium, buffer and/or solubilizing agent can be used to facilitate the formation of complex.

Any foreign substance can be used in the preparation of a complex subject that the substance can binds to PAA in the carrier of the present invention electrostatically. Examples of foreign substance include a drug; contrast medium; polynucleotides such as DNA, RNA, oligonucleotide, gene; peptide, and the like which are useful in the treatment or diagnosis of target organ, especially liver. It was found that when the foreign substance is a polypeptide, the carrier advantageously retains it, stabilizes double- or triple-stranded DNA, solubilizes the complex. There are no limitations about the length or the structure of the DNA, and liner, circular, single- or double-stranded DNA is usable. DNA derivatives such as phosphodiester, phosphorothioate, or the like are also available.

Examples of drugs include ascorbic acid, acetazolamide, azosemide, adenosine triphosphate, anethol trithion, amidotrizoic acid, aminoethanesulfonic acid, aminophylline, alglucerase, alprostadil, ampicillin, iotalamate meglumine, imipenem, cilastatin, interferon-α, interferon-β, indocyanine green, ursodesoxycholic acid, etacrynic acid, osalmid, liver hydrolysate, liver extract, flavin, adenin dinucleotide, freeze-dried inactivated tissue culture hepatitis A vaccine, zidovudine, canrenoate, xylitol, glycyrrhizic acid, methionine, cysteine, glucuronolactone, glucuronamide, glucuronate, immunoglobulin, prednisolone phosphate, predonizolone succinate, chenodeoxycholic acid, cyclophosphamide, cytarabine, antimony tartrate, zinostatin stimalamer, spironolactone, sulfobromophthalein, cefodizime, cefoperazone, sulbactam, ceftazidime, placenta extract, tacrolimus hydrate, tiopronin, hepatitis B vaccine, human serum albumin, tegafur uracil, sorbitol, dexamethasone, dexamethasone phosphate, dehydrocholic acid, tocamphyl, triamcinolone diacetate, pneumococcus vaccine, panipenem betamipron, hydrochlorothiazide, hydrocortisone succinate, hydrocortisone phsophate, hydroflumethiazide, fluorouracil, furosemide, flpropione, glucose, phenylpropanol, hymecromone, trepibutone, bumetanide, praziquantel, protoporphyrin, propagerumanium, betamethasone valerate, benzylhydrochlorothiazide, penicillamine, penflutizide, polyenphosphatidyl choline, malotilate, dexamethasone metasulfobenzoate, methyclothiazide, methypredonizolone, metolazone, mefruside, meropenem trihydrate, folic acid, latamoxef, cefpirome, betamethasone phosphate, and thioctic acid.

The carrier of the present invention is useful as a carrier for gene therapy which can deliver DNA or the like to a target organ especially liver safely and efficiently.

Examples of gene therapy to which the present carrier applicable include gene transfer or anti-gene therapy for treating liver diseases as shown below:

Liver fibrogenesis and cirrhosis: inhibition of pro-fibrogenesis cytokine (antisense for TGF-beta, or transfer of anti-TGF-beta gene, docorin); fibrolysis (transfer of metallomatrix protease (MMP) genes);

Liver carcinoma: inhibition of tumor angiogenesis (antisense for VEGF receptors);

Organ-specific tolerance: antisense for adhesion molecules, i.e., ICAM-1 or specific killing of graft specific cytotoxic T cells [CTL] by transferring the Fas ligand gene; Xenotransplantation: inhibition of activation of SEC by preventing transactivation of NF-kB by introducing a decoy that is a double-stranded DNA designed to have high affinity for NFkB; and Virus infection: anti-HIV therapy by introducing HIV-specific ribozymes (it has been shown that SEC is permissible by HIV).

Although the quantity of the gene to be coupled to the carrier is not limited, about 0.1 to 100 μmoles of carrier is used per 1 μmole of nucleic acid. The carrier of the present invention is applicable to any types of gene therapy, including the "ex vivo" method for autotransplantation where a complex containing a given gene is introduced into a target cell previously removed from a patient and the cell is then introduced to the patient, and "in vivo" method where a complex is introduced to a patient directly. Further, the carrier of the present invention is applicable to the augmentation gene therapy where a normal gene is introduced to a patient while remaining the causative (abnormal) gene as it is, or the replacing gene therapy where a normal gene is substituted for the causative gene.

By the use of the present carrier, it is possible to treat a patient by introducing a structural gene encoding a therapeutically effective protein and allowing to express it in the target cells. It is also possible to suppress the expression of a give gene through the introduction of an antisense strand. Further, the carrier of the present invention is usable to deliver ribozyme, triplex, aptamer, or the like to target organ.

The complex containing a foreign substance of the present invention can be administered orally or parenterally. However, the administration is preferably done in parenteral manner such as injection. In the case of injection, the complex of the present invention can be formulated for intravenous, intraarterial, intramuscular, hypodermic injection, and the like. In the formulation, appropriate additives used in the art such as preservative, pH adjusting agent or the like can be added. The dosage of the complex of the present invention varies depending on the age, conditions and the like of a patient to be treated, as well as the mode and purpose of the treatment. The usual daily dosage, however, could be about 0.1 μg/kg to 100 mg/kg, preferably, about 1 μg/kg to 50 mg/kg, when a complex containing nucleic acid is injected.

The present invention is further described in the following Examples, but should not be construed to limiting the scope of the present invention.

EXAMPLE 1

Synthesis of Hyaluronate-grafted Poly-(L-lysine Copolymer (HA-g-PLL or PLL-g-HA

The HA (Mn, $3.2 \times 10^5$ Denkikagaku Kogyo (Tokyo, Japan)) was enzymatically digested by hyaluronidase to obtain low molecular weight fragments. Hyaluronidase (20 mg) was added to a solution containing 1 g of the HA in 100 ml water. Hyaluronidase was obtained from Sigma (Type 1-S, St. Louis, Mo.). The solution was stirred at 50° C. for 1 h, boiled for 5 min to terminate the reaction, and allowed to cool to room temperature. After removing denatured hyaluronidase by filtration through a 0.45 μm filter (New Steradisc 25, KURABO, Osaka, Japan), the solution was lyophilized. The molecular weight of the digested HA fragments was determined by gel permeation chromatography (GPC) on ultrahydrogel 500 and 250 (Japan Waters, Tokyo, Japan) connected to a light scattering detector (DAWN-DSP, Wyatt Technology, Santa Barbara, Calif.) and a refractive index detector (Model 830-RI, JASCO, Tokyo, Japan).

Figure 1:
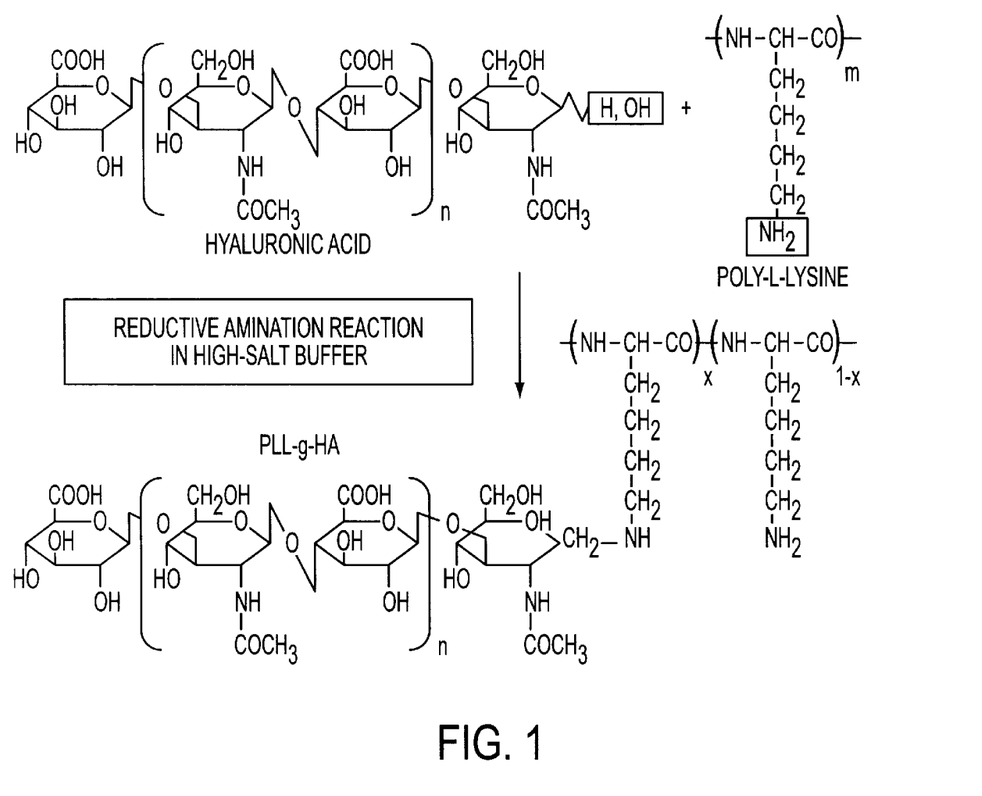

The HA fragments (Mn $1.5 \times 10^4$) thus obtained were conjugated to PLL by a reductive amination reaction using sodium cyanoborohydride ($NaB_3CN$) as a reductant. Poly-(L-Lysine)hydrobromide (PLL) with number-average molecular weight (Mn) of $4.6 \times 10^4$ was purchased from Peptide Institute (Osaka, Japan). Equal amounts of HA and PLL, 100 mg each, were dissolved in 15 ml borate buffer (0.1 M, pH=8.5) containing 1 M NaCl. A $NaBH_3CN$ solution (376.8 mg, in 5 ml borate buffer) was added directly to the mixture. The reaction mixture was stirred and incubated at 40° C. for 48 h. The resulting copolymer (hyaluronate-grafted poly-(L-Lysine): PLL-g-HA) was isolated from unreacted HA fragments by dialyzing for 3 days against 1 M NaCl through membranes with a molecular weight limit of 25,000 (Spectrapor 7 membrane, Spectrum, Tex.) and lyophilized. The structural formula of the graft copolymer is shown in FIG. 1.

EXAMPLE 2

Confirmation of Hyaluronate-grafted-poly-(L-Lysine) Copolymer

Figure 2:
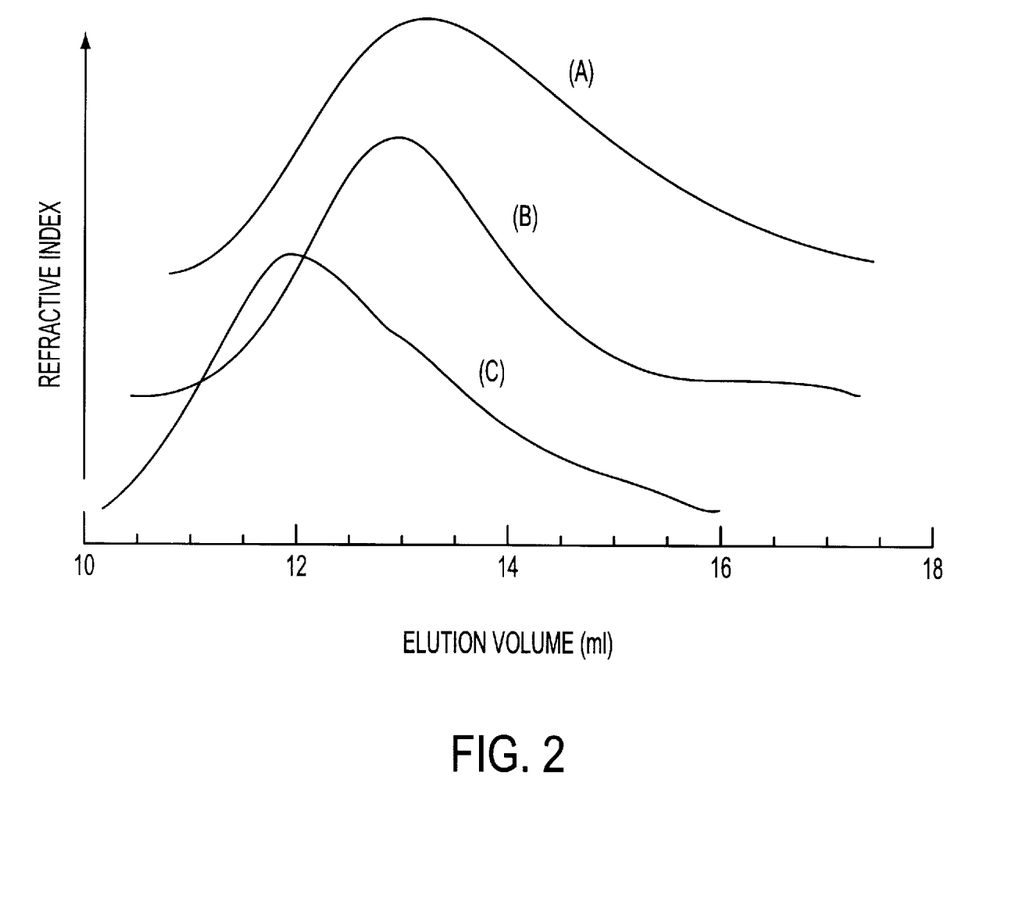

Molecular weights of the HA fragments, PLL and the synthesized PLL-g-HA were determined by GPC on Ultrahydrogel 500 and 250 in a column of 7.8 mm×300 mm (internal diameter×height) connected to a light scattering detector and a refractive index detector. All data were obtained using dn/dc=0.145 ml/g. Eluent:0.5 M $CH_3COOH$ and 0.3 M $Na_2SO_4$; flow rate:1.0 ml/ml. Since HA is a polyanion, inter-polyelectrolyte complex (IPC) that could disturb the conjugating reaction might be formed in its mixture with PLL. Such IPC formation could be suppressed in high ionic strength media (Perals, J. C. et al., Eur. J. Biochem. 226, 255–266 (1994); Olines, D. -E., et al., J. Mol. Biol. 24, 157–176, (1967)). Thus, to avoid IPC formation and allow the reaction to proceed in a homogeneous system, the conjugating reaction between PLL and HA was carried out in PBS containing 1 M NaCl. FIG. 2 shows the results of GPC measurements for HA (A), PLL (B), and the resulting PLL-g-HA copolymers (C). An increase in molecular weight, as evidenced by a shift of the molecular weight distribution of PLL-g-HA toward the left, indicated successful conjugation between PLL and HA. Further, the graft copolymer was found to be almost completely isolated from unreacted HA by dialysis as seen from the GPC profile (FIG. 2). The Mn of the PLL-g-HA was determined as $6.3 \times 10^4$ by GPC.

Figure 10:
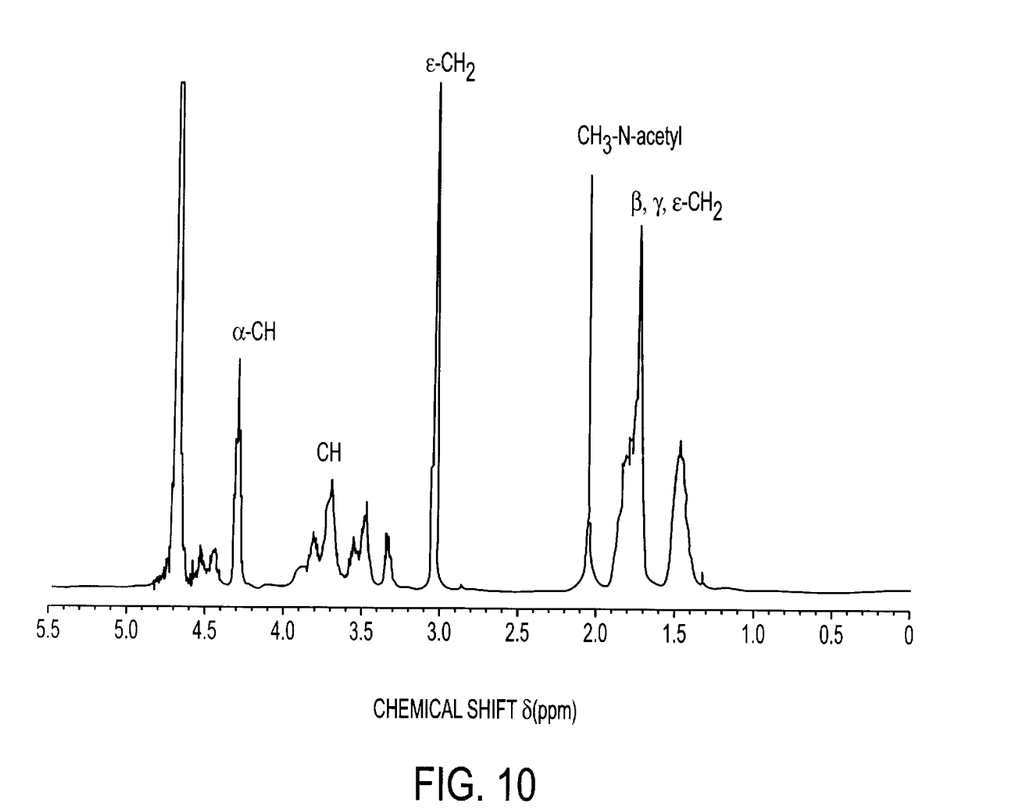

Composition of the copolymer was determined from $^1$H-NMR (UNITY 400 plus spectrometer, Varian, Palo Alto, Calif.) spectra (400 MHZ) in D20 containing 500 mM NaCl. The 1H-NMR spectra of the copolymers involved characteristic signals of both PLL: δ=1.4–1.9 (β, γ, δ—$CH_2$), δ=3.0 (ε—$CH_2$), δ=4.3 (α—CH) and HA: δ=3.0–4.0 (CH), δ=2.0 ($CH_3$—N-acetyl) moieties. Composition of the copolymer was determined by comparing peak areas of N-acetyl signal of HA and g-methylene signal of PLL to be 57 wt % PLL and 4 wt % HA, which meant that HA chains were grafted onto an average of one of every 150 lysine units (0.67 mol %, 50 wt %) with a coupling efficiency of 47% (FIG. 10).

In accordance with the process described above, the PLL-g-HA copolymers in Table 1 were prepared.

TABLE 1

| HA m.w. | Grafting rate (%) | |
|---|---|---|
|  | (mol %) | (weight %) |
| 4.6K | 5.64 | 67 |
| 15.0K | 0.59 | 53 |
| 1.9K | 7.25 | 52 |
| 1.9K | 11.56 | 63 |

EXAMPLE 3

Effect of PLL-g-HA on dsDNA Melting

Figure 11:
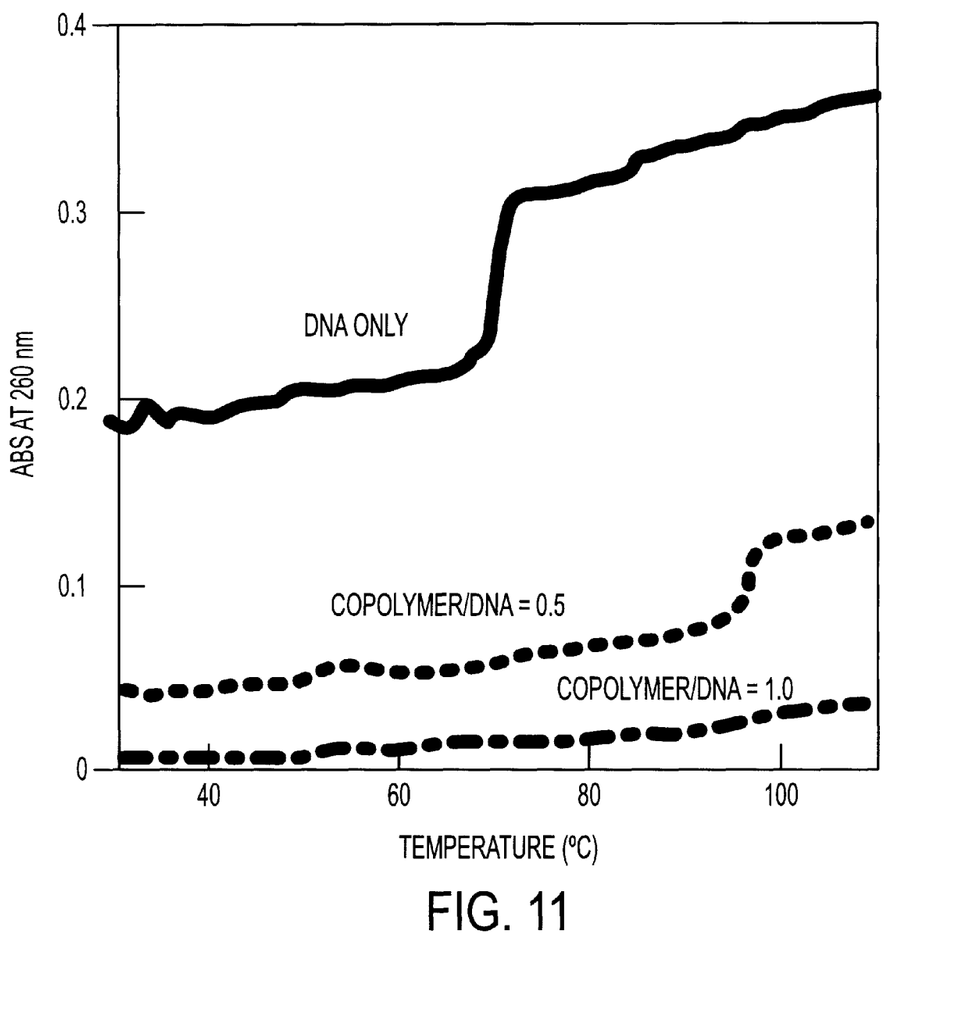

The PLL-g-HA copolymer considerably stabilized DNA duplex. The stabilizing effect of the copolymers on DNA duplex was evaluated on the basis of thermal melting profiles obtained by measuring absorbance at 260 nm with a UV spectrometer. FIG. 11 shows the UV-Tm profile of DNA duplex in the presence or absence of PLL-g-HA. DNA (poly-d[A]d[T] Pharmacia Biotech, Uppsala, Sweeden) was dissolved in 150 mM NaCl containing 10 mM sodium phosphate (pH=7.2) and 0.1 mM EDTA. To a DNA (poly-d[A]d[T] solution was added the PLL-g-HA in such a manner that the ratio of the charge of the copolymer and that of DNA ([amino group]$_{copolymer}$/[phosphate group]$_{DNA}$=P/D charge ratio) is 0.5 and 1.0 to evaluate the relationships between the stabilizing effect of the copolymer and the ratio thereof in the resultant complex. The mixture was diluted with the same buffer to make the final concentration of DNA(poly-d[A]d[T]) 14.5(bp)μm/L with the same buffer, the mixture were heated at 110° C. for 30 min, cooled to room temperature, and allowed to stand for 16 h. The UV-Tm curves were recorded at 0.2 K/min with a DU-640 spectrometer equipped with a micro-Tm apparatus.

At physiological ionic strength, the transition at 70° C. shows the melting of a dsDNA to ssDNA. In the presence of excess DNA(poly-d[A]d[T]) over copolymer, only one transition was observed at 95° C. When the P/D charge ratio is 1.0, the transition did not occurred. The results indicates that the PLL-g-HA is effective in stabilization of duplex.

EXAMPLE 4

Preparation of PLL-g-HA/DNA Complex pSV β-Gal (Promega, Madison, Wis.) (1–100 μg/ml) was mixed with various amounts of PLL-g-HA (5 mg/ml in PBS) in PBS containing 8.1 mM $Na_2HPO_4$, 2.68 mM KCl, 1.47 mM $KH_2PO_4$ and 1 M NaCl and allowed to stand at 4° C. for at least 1 h. The mixtures were then diluted to a final NaCl concentration of 154 mM with NaCl-free PBS and allowed to stand at 4° C. for at least 1 h. The mixtures were then diluted to a final NaCl concentration of 154 mM with NaCl-free PBS and allowed to stand at 4° C. for more than 24 than 24 h before use.

EXAMPLE 5

Confirmation of PLL-g-HA/DNA Complex

To determine the proportions of the PLL-g-HA that should be mixed with plasmids to optimize the DNA content of the complex, increasing amounts of PLL-g-HA were added to a fixed amount (1 μg) of PSV β-Gal at copolymer to DNA charge ratios ([amino group]$_{copolymer}$/[phosphate group]$_{DNA}$: P/D charge ratios) of 0.1, 0.5, 0.7, 1.0 and 1.2, all in 1 M NaCl. Samples were allowed to stand for 12 h at 4° C. and diluted to 154 mM NaCl with double distilled water.

Figure 3:
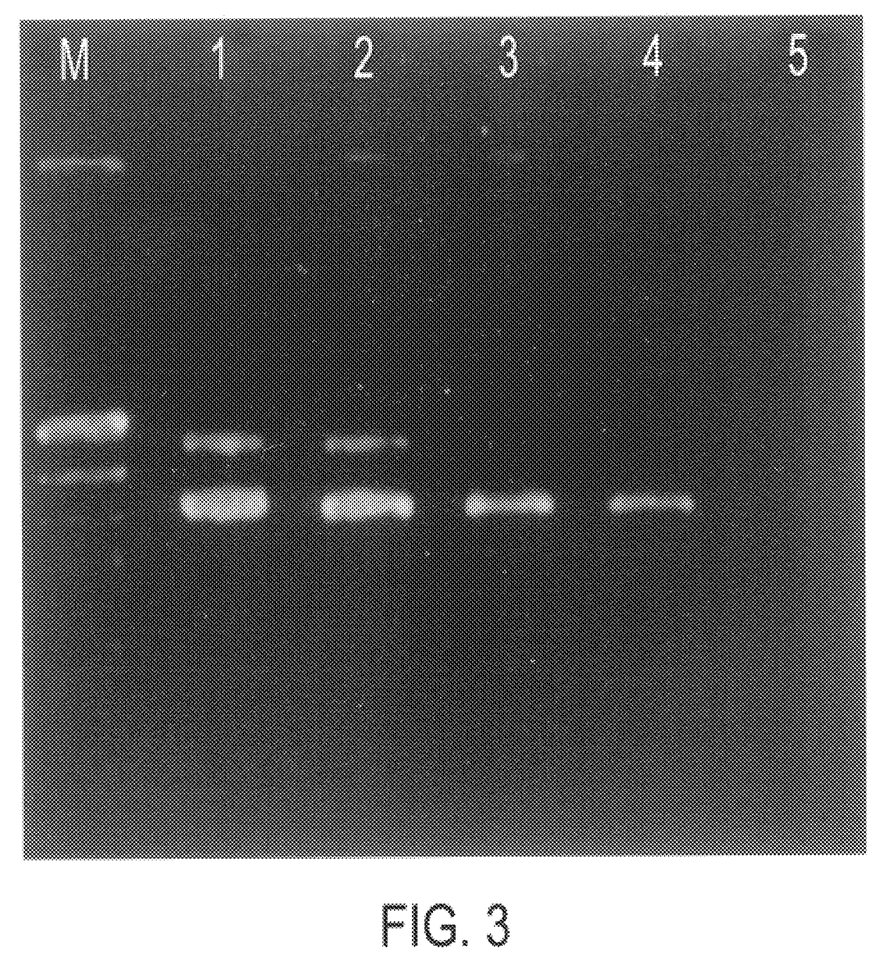
Figure 4:
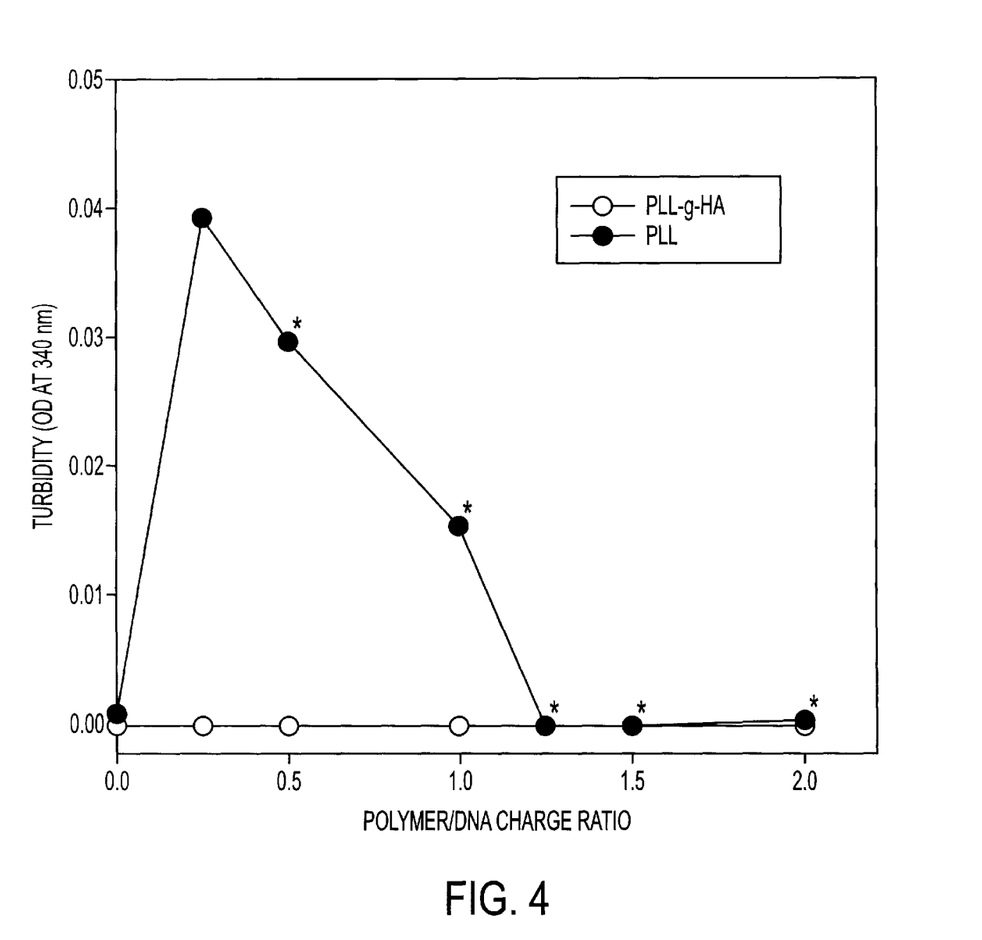

Complex formation between PLL-g-HA and DNA was assessed with a gel retardation assay. Increasing the proportion of the PLL-g-HA copolymer in the DNA samples affected plasmid DNA migration in an agarose gel as shown in FIG. 3. Samples containing an equal amount of DNA (100 ng) were then electrophoresed on a 0.8% agarose gel in Tris-acetate/EDTA buffer followed by staining with ethidium bromide to visualize DNA. (M, λ/Hind III digest as a molecular size marker; P/D ratio of each lanes are: lane 1, 1:0.1; lane 2, 1:0.5; lane 3, 1:0.7; lane 4, 1:1.0; and lane 5, 1:1 2). As the proportion of PLL-g-HA-copolymer in the samples increased, there was a decrease in staining intensity of DNA that migrated in the gel as seen in Lane 1 to 5, at P/D charge ratios ranging from 0.1 to 1.2. This result indicates that progressively increasing amounts of DNA were retained by the PLL-g-HA copolymer as the proportion of PLL-g-HA increased in the samples. Moreover, the titration point representing the minimum proportion of PLL-g-HA required to retard completely the DNA at a physiological ionic condition (154 mM NaCl) occurred at a P/D charge ratio of approximately 1 (FIG. 3). Therefore, complexes composed of this ratio (1:1) of components were subsequently experimented in vivo. Following the procedure described above, PBS solutions containing 50 μg/ml DNA and various proportions of PLL-g-HA or PLL were prepared. The turbidity of the solutions was determined by measuring absorbance at 340 nm with a spectrophotometer (Beckman DU 640, Fullerton, Calif.). FIG. 4 shows the results of the turbidity measurement of PBS solutions containing various ratios of PLL or PLL-g-HA and DNA. Open circle: PSVβ-Gal and PLL-g-HA; closed circle: PSV β-Gal and PLL. In this experiment, the PLL-g-HA (PLL, Mn: $7.2 \times 10_4$; HA, Mn: $3.8 \times 10^4$; and grafting rate 0.74 mol %, 69 wt %) was used. (The symbol "*" means that precipitation was observed.) The PLL homopolymer caused significant turbidity at a charge ratio≦0.25 and bulky precipitates at a charge ratio≦0.5. In contrast, neither turbidity nor precipitation was observed in PLL-g-HA/DNA mixtures over the charge ratio from 0 to 2 (FIG. 4). The results indicated that IPC formation between the graft copolymer and DNA exhibited minimal self-aggregation, explaining the highly soluble nature of the complex.

EXAMPLE 6

Organ Distribution of PLL-g-HA/DNA Complex

To ascertain if the PLL-g-HA/DNA complexes were delivered to the liver in vivo, the following experiments were carried out. An expression plasmid encoding lacZ (pSVβ-galactosidase control vector (pSVβ-Gal, Promega, Madison, Wis.) was grown in *Escherichia coli*, isolated and purified by a standard method. For the in vivo uptake study, the plasmid pSVβ-Gal was labeled with $^{32}p$ by the multiprime method with a commercial kit available (Random Primer DNA Labeling Kit version 2, Takara, Japan). Groups of Wistar rats weighing 200–500 g were injected intravenously via the tail vein with the $^{32}p$-labeled pSVβ-Gal (90 μg) complexed to the PLL-g-HA in 500 μl saline. After 1 h, rats were anesthetized with ether, their abdominal cavity opened, blood was sampled, and perfused briefly with saline, and, liver, spleen, gut, heart, lung, kidney, and thymus were obtained. The tissue samples were weighed, homogenized in saline, solubilized with a tissue solubilizer (Soluene-350, Packard Instrument, Meriden, Conn.), mixed with aqueous scintillant (High-Ionic Fluor, Packard) and counted on a liquid scintillation analyzer (IPI-CARB 1500, Packard).

Figure 5:
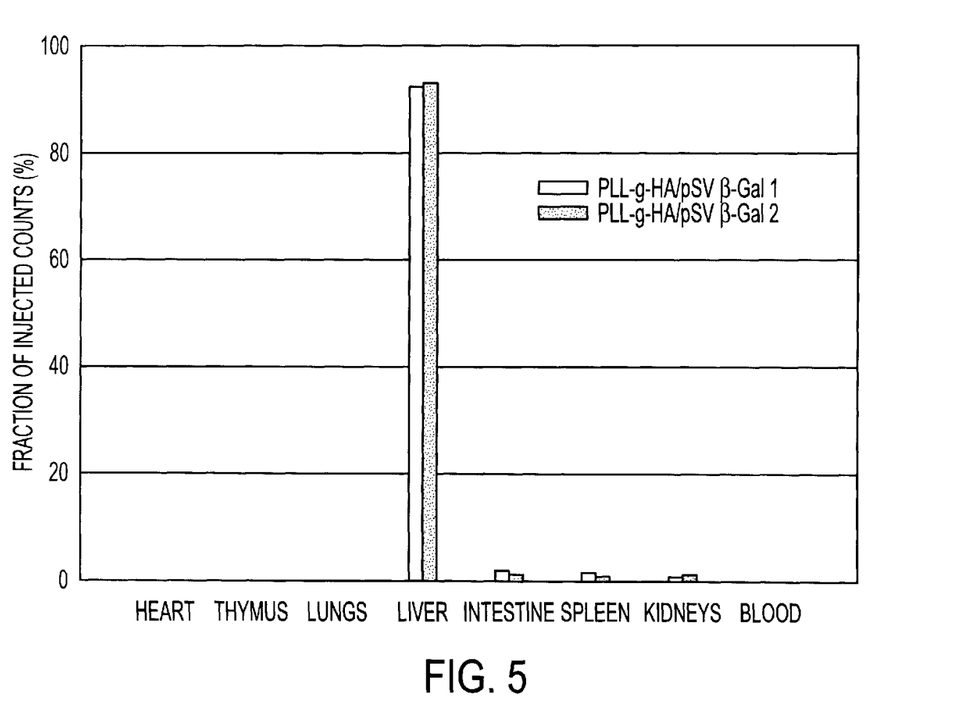

Organ distribution of the radiolabeled pSVβ-Gal that had been injected in equal quantities ($7.5 \times 10^6$ counts) is shown in FIG. 5. The FIG. 5 shows the results of two separate experiments. When the plasmid was complexed to PLL-g-HA, the PLL-g-HA/DNA complex was almost exclusively delivered to the liver: 1 h after injection, more than 90% of the injected counts were detected in the liver. The residual counts distributed in other organs were as fellows: 2.5% in intestine, 2% in spleen, 1.5% in kidney, and <<1% in heart, thymus, lung and blood. A similar result was seen 3 hours postinjection (data not shown).

EXAMPLE 7

Determination of Ability of PLL-g-HA in Targeted Delivery to Liver

The ability of PLL-g-HA in the organotropic delivery was evaluated as follows. Thus, to detect the transgene in the liver after in vivo transfection, 90 μg of pSVβ-Gal, either complexed to PLL-g-HA or alone, was injected intravenously. After 3 h, rats were anesthetized with ether, the abdominal cavity were opened, and livers were perfused briefly with saline, then homogenized in a solution containing 154 mM NaCl and 10 mM EDTA. The cytosolic fraction was prepared by ultracentrifugation (20,000 g, 15 h) with a Beckman ultracentrifuge (TL-100, Palo Alto, Calif.) according to the conventional method (Chowdhury, N. R. et al., J. Biol. Chem. 168, 11265–11271, 1993). The transgene was extracted from the cytosolic fractions by phenol, three times, phenol/chloroform (1:1, v/v), chloroform, ethanol-precipitated, and resuspended in a Tris-EDTA buffer.

Polymerase chain reaction (PCR) to amplify the plasmid DNA was performed using a standard kit (GeneAmp, Parkin, Elmer, Norwalk, Conn.). Primer sets used were as follows:
forward: 5'-TACTGTCGTCGTCCCCTCAA-3' SEQ ID NO: 1 and
reverse: 5'-ATAACTGCCGTCACTCCAAC-3' SEQ ID NO: 2

Figure 7:
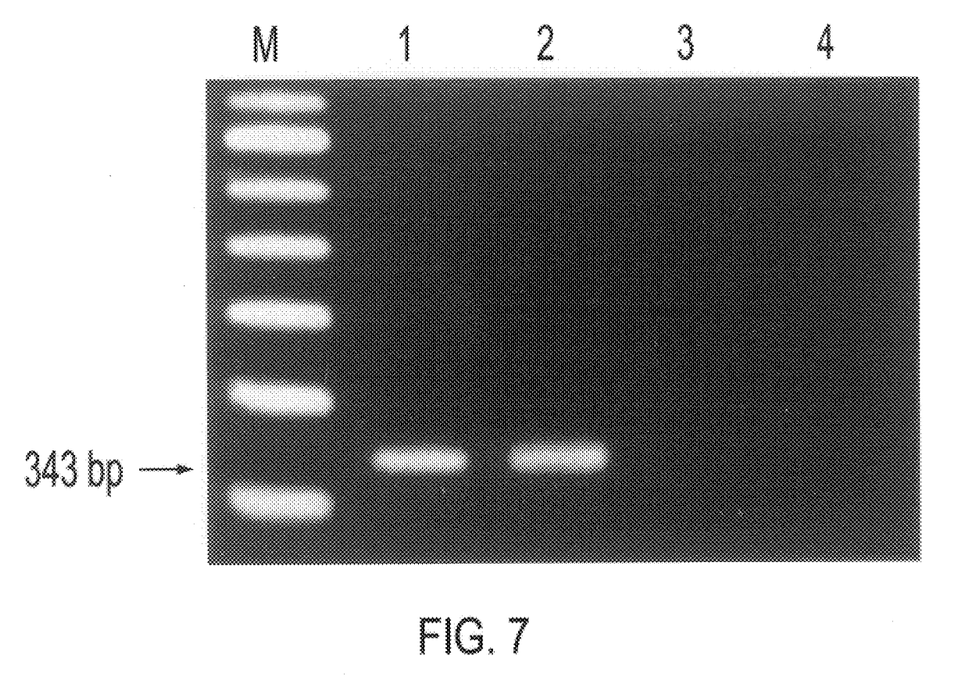

The reaction mixture (50 μl) contained 5 μl samples, 25 pmol each of the oligonucleotide primers, 1.5 mM $MgCl_g$, 200 μM dNTP, and 1.25 U of Taq DNA polymerase (Takara, Kyoto, Japan). All reactions were carried ont at 94° C. (30 s), 54° C.(30 s) and 72° C.(90 s) for 30 cycles (GeneAmp 2400, Perkin Elmer). The PCR products were separated by agarose gel electrophoresis. FIG. 7 illustrates the results of PCR amplification of the cytosolic fractions of the liver homogenate. FIG. 7 shows the results obtained in two separate experiments in each group. In lanes 1 and 2, the presence of the transgene was demonstrated 3 h after in vivo transfection as a single band of the 343 bp PCR product when the pSVβ-Gal plasmid was administered in a PLL-g-HA-complexed form, whereas PCR failed to detect the transgene in a sample prepared from the liver of rat injected with pSVβ-Gal alone (lanes 3 and 4). The transgene was detectable up to 24 h after transfection with the PLL-g-HA/DNA (see, below and FIG. 8).

EXAMPLE 8

Confirmation of Gene Expression

To determine if the PLL-g-HA/DNA complexes were expressed after delivered into the liver in vivo, the following experiments were carried out.

Groups of Wistar rats weighing 200–250 g were injected intravenously via the tail vein with the unlabeled pSV-β-Gal (90 μg) complexed to the PLL-g-HA in 500 μl saline or plasmid alone. After 24, 48, 72 hours, rats were anesthetized with ether, the abdominal cavity was opened, and livers were perfused briefly with saline, and harvested. Total hepatic RNA, isolated by Isogen (Nippon Gene, Japan) following in vivo transfection, was reverse transcribed with a kit (You-Prime First Strand Beads, Pharmacia biotech) and the resultant cDNA was amplified by PCR. One microliter of the cDNA pool was amplified using the primers described above. For comparison with the amount of the transgene remaining in the liver tissue, the same RNA samples not converted to cDNA by reverse transcriptase were also amplified by PCR. The PCR products were separated by agarose gel electrophoresis.

Figure 8:
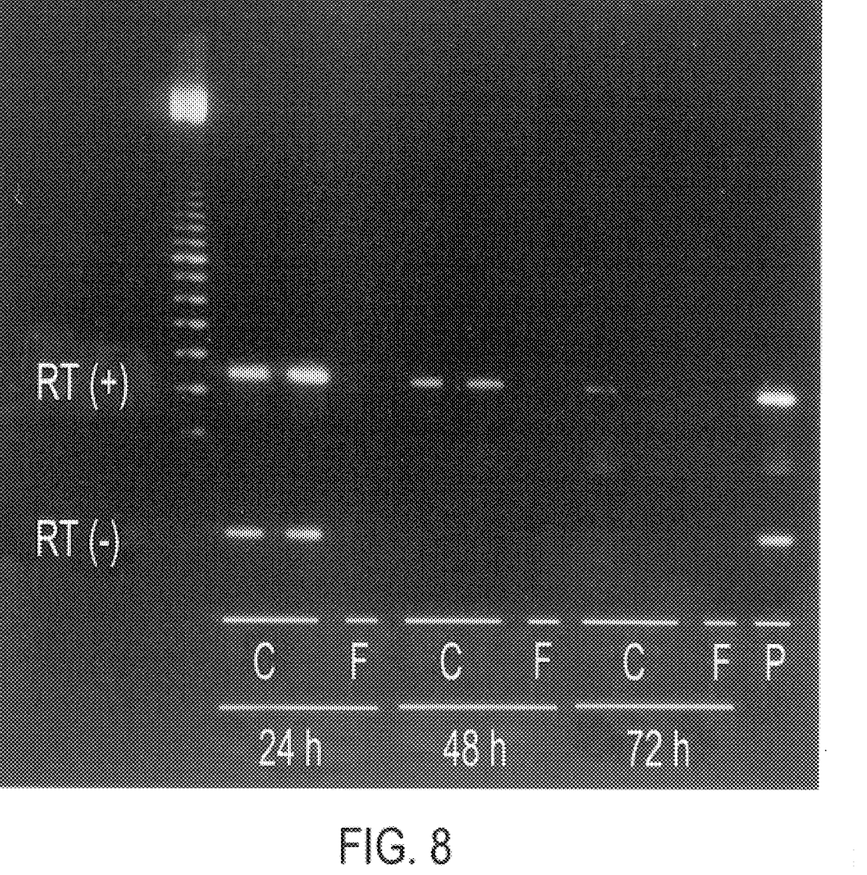

Presence of the lacZ mRNA in the livers of rats transfected with pSVβ-Gal, either complexed to PLL-g-HA or alone, was determined by RT-PCR. The β-Gal mRNA could be detected up to 72 hours after transfection in the group infected with the PLL-g-HA/pSVβ-Gal complex (FIG. 8). In contrast, no β-Gal mRNA was detected even at 24 hours post-transfection when administered with pSVβ-Gal alone. It should be noted that in the absence of reverse transcription, the pSVβ-Gal DNA was only detected 24 h after transfection, however, no plasmid DNA was amplified beyond a time period of 24 hours. As a control, the same RNA samples not converted to cDNA were also amplified by PCR. The results are shown in FIG. 8. Upper panel (RT(+)): lane 1, 100 bp ladder; lanes 2 and 3 (C): 24 h after transfection with PLL-g-HA/pSVβ-Gal; lane 4 (F): 24 h after transfection with free PLL-g-HA/pSVβ-Gal; 24 h after transfection with PLL-g-HA/pSVβ-Gal; lanes 5 and 6(C): 48 h after transfection with PLL-g-HA/pSVβ-Gal; lane 7 (F): 48 h after transfection with free PLL-g-HA/pSVβ-Gal; lanes 8 and 9(C): 72 h after transfection with PLL-g-HA/pSVβ-Gal; lane 10 (F), 72 h after transfection with free PLL-g-HA/pSVβ-Gal; lane 11(P): positive control (10 pg of pSVβ-Gal was amplified). Lanes 2–3, 5–6 and 8–9 show the results of two separate experiments. Lower panel (RT(−)): same conditions as upper panel except that the samples were not reverse-transcribed.

The following experiments were carried out using β-galactosidase activity. Seventy-two hours after injection of either 90 μg of pSVβ-Gal, or an equal amount of pSVβ-Gal in a PLL-g-HA-complexed-form, rats were anesthetized with ether, the abdominal cavity was opened, and the liver was perfused briefly with saline, and harvested, frozen in liquid nitrogen and cut into 8 μm sections. Sections were fixed with 1% glutaraldehyde, washed with PBS, and incubated at 37° C. for 1 h in PBS containing 33 μM $C_{12}FDG$, for detection of lacZ gene expression, a fluorogenic β-galactosidase substrate, 5-dodecanoylamino-fluorescein di-β-galactopyranoside ($C_{12}FDG$, Molecular Probes, Eugene Oreg.) was used, and viewed under an epifluorescent microscope with an appropriate filter set. Original magnification, ×200.

Figure 9:
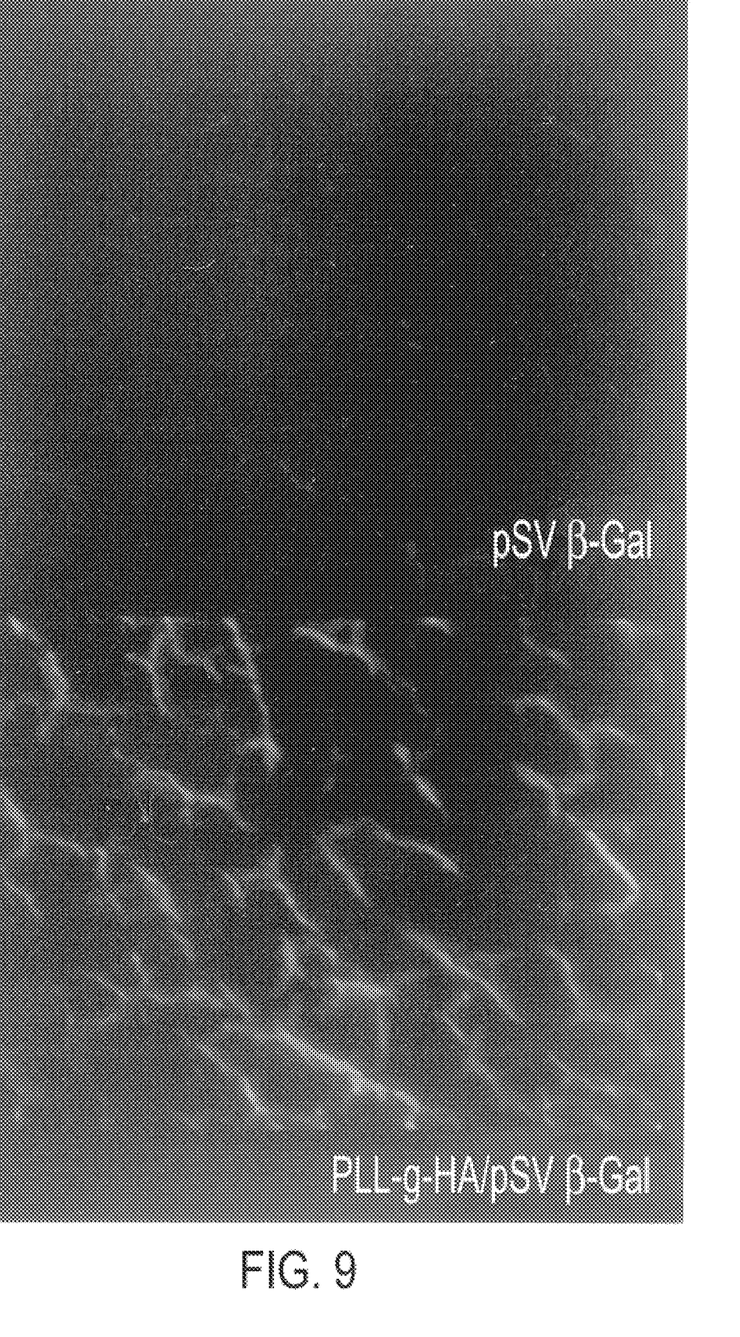

FIG. 9 shows histological detection cells expressing β-galactosidase in the liver lobule 72 h after in vivo transfection. In control, in which pSVβ-Gal alone was administered, no cells expressing β-galactosidase were observed (upper panel). In marked contrast, a large number of cells expressing β-Gal were detected in the sinusoidal endothelial cells when transfected with an equal amount of pSV-β-Gal in a PLL-g-HA-complexed form (lower panel).

EXAMPLE 9

Confirmation of Gene Delivery

To determine if the PLL-g-HA/DNA complexes retained their ability to be delivered to the liver in vivo, the following experiments were carried out. To assess the distribution of the PLL-g-HA/DNA complexes in the liver lobules, groups of Wistar rats weighing 200–250 g were injected intravenously via the tail vein with the an FITC-labeled oligonucleotide (18 mer, 90 μg as DNA) complexed to the PLL-g-HA or plasmid alone. Fifteen minutes post-injection, rats were anesthetized with ether, the abdominal cavity was opened, and livers were perfused briefly with saline, harvested, and frozen in liquid nitrogen and cut into 8 μm sections. Sections were observed under an epifluorescent microscope (Olympus, Tokyo, Japan) with a filter set for FITC. Original magnification: ×100 and ×200 (inset).

Figure 6:
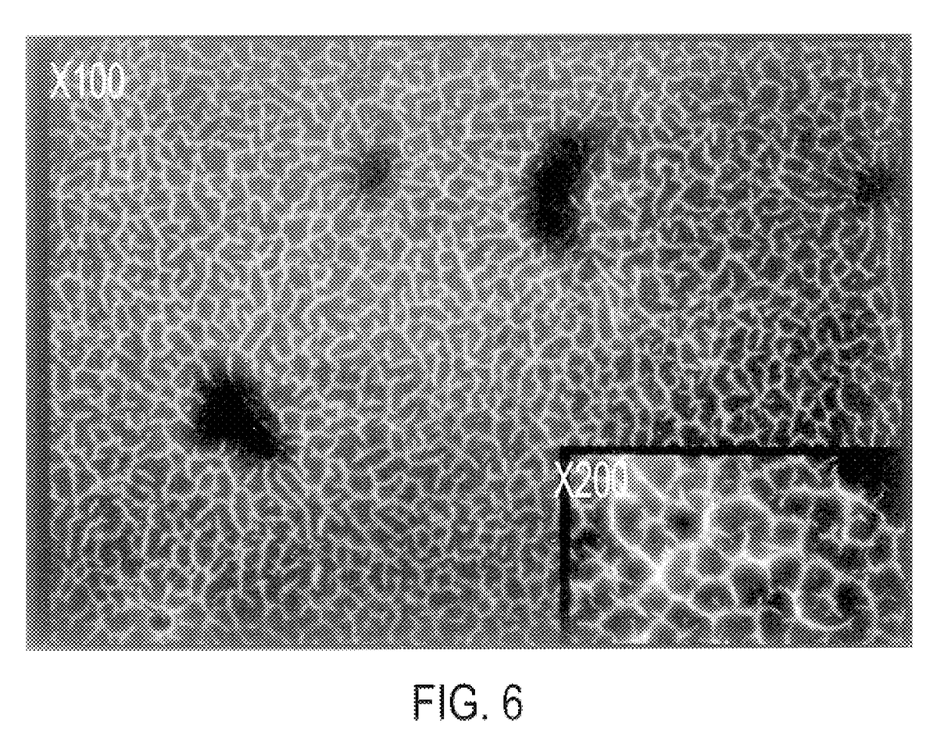

Distribution of the PLL-g-HA/DNA complex in the liver lobule is depicted in FIG. 6. Fifteen minutes after the administration of the PLL-g-HA complexed to FITC-labeled DNA, fluorescence was localized exclusively in sinusoidal endothelial cells. In addition, administration of 100-fold excess of HA (as compared to the HA amounts of the PLL-g-HA/DNA) just before transfection with the PLL-g-HA/DNA greatly diminished intensity of FITC fluorescence in sinusoidal endothelial cells.

6. A complex which is formed through the electrostatic binding between the foreign substance and the carrier of claim 1.

7. The complex of claim 6 wherein the electrostatic binding is formed through a positively charged part of the polymer main chain of the graft copolymer and a negatively charged part of the foreign substance.

8. The complex of claim 6 wherein the foreign substance is selected from the group consisting of polynucleotide, drug and contrast medium.

9. The complex of claim 6 wherein the organ is liver.

10. The carrier of claim 1, wherein the weight percent of hyaluronic acid in the graft copolymer is from 5 to 90 wt %.

11. A graft copolymer comprising (1) a polymer main chain which has a region capable of binding to a foreign substance electrostatically and has one or more monomer units having a side chain with an amino or an imino group capable of coupling to hyaluronic acid and (2) hyaluronic

---

---

What is claimed is:

1. A carrier for delivering a foreign substance to a target organ having receptors for hyaluronic acid which comprises a graft copolymer comprising (1) a polymer main chain which has a region capable of binding to the foreign substance electrostatically and has one or more monomer units having a side chain with an amino or an imino group capable of coupling to hyaluronic acid and (2) hyaluronic acid grafted to the polymer main chain; said polymer main chain comprising amino acids or amino acid derivatives coupled through peptide bonds.

2. The carrier of claim 1 wherein the monomer units are selected from the group consisting of lysine, ornithine, arginine and derivatives thereof.

3. The carrier of claim 1 wherein the region capable of binding to the foreign substance electrostatically comprises monomer units selected from the group consisting of lysine, ornithine, arginine and derivatives thereof to the extent sufficient for the formation of electrostatic binding.

4. The carrier of claim 1 wherein the polymer main chain comprises polylysine.

5. The carrier of claim 1 wherein the grafting rate of hyaluronic acid in the graft copolymer is from 0.01 to 50 mol %.

acid grafted to the polymer main chain; said polymer main chain comprises amino acids or amino acid derivatives coupled through peptide bonds.

12. The graft copolymer of claim 4, wherein the monomer units are selected from the group consisting of lysine, ornithine, arginine and derivatives thereof.

13. The graft copolymer of claim 11, wherein the region capable of binding to the foreign substance electrostatically comprises monomer units selected from the group consisting of lysine, ornithine, arginine and derivatives thereof to an extent sufficient for the formation of electrostatic binding.

14. The graft copolymer of claim 11, wherein the polymer main chain comprises polylysine.

15. The graft copolymer of claim 4, wherein the grafting rate of hyaluronic acid in the graft copolymer is from 0.01 to 50 mol %.

16. The graft copolymer of claim 11, wherein the weight percent of hyaluronic acid in the graft copolymer is from 5 to 90 wt %.

* * * * *